(12) United States Patent
Lee et al.

(10) Patent No.: US 12,186,443 B2
(45) Date of Patent: Jan. 7, 2025

(54) APPARATUS FOR STERILIZATION OF INSIDE OF VEHICLE USING DRONE

(71) Applicants: Hyundai Motor Company, Seoul (KR); Kia Corporation, Seoul (KR)

(72) Inventors: Jae Seung Lee, Hwaseong-si (KR); Dae Hee Lee, Incheon (KR); Kyu Hoon Cho, Suwon-Si (KR); Seung Sik Han, Hwaseong-Si (KR); Yong Hyun Nam, Anyang-Si (KR); Chung Sik Yim, Anyang-Si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 823 days.

(21) Appl. No.: 17/353,385

(22) Filed: Jun. 21, 2021

(65) Prior Publication Data
US 2022/0152254 A1 May 19, 2022

(30) Foreign Application Priority Data

Nov. 13, 2020 (KR) .......................... 10-2020-0151536

(51) Int. Cl.
*A61L 2/24* (2006.01)
*A61L 2/10* (2006.01)
(Continued)

(52) U.S. Cl.
CPC .................. *A61L 2/24* (2013.01); *A61L 2/10* (2013.01); *A61L 2/22* (2013.01); *B64D 1/18* (2013.01); *B64D 47/02* (2013.01); *B64F 5/40* (2017.01); *B64U 30/299* (2023.01); *B64U 50/14* (2023.01); *G02B 5/0891* (2013.01); *G02B 26/103* (2013.01); *A61L 2202/11* (2013.01); *A61L 2202/14* (2013.01); *A61L 2202/15* (2013.01); *A61L 2202/16* (2013.01); *A61L 2202/25* (2013.01); *B64D 2203/00* (2013.01);
(Continued)

(58) Field of Classification Search
CPC .... B64U 10/13; B64U 30/20; B64U 2101/00; B64U 2101/10; B64U 2101/29; A61L 2/10; A61L 2/22; A61L 2202/16; A61L 9/14; A61L 9/20
See application file for complete search history.

(56) References Cited

U.S. PATENT DOCUMENTS

2018/0118337 A1* 5/2018 Viel ...................... G05D 1/0094
2018/0155026 A1* 6/2018 Policicchio ............... A61L 9/14
(Continued)

FOREIGN PATENT DOCUMENTS

KR  10-1860938 B1  5/2018

*Primary Examiner* — Jennifer Wecker
*Assistant Examiner* — Brady C Pilsbury
(74) *Attorney, Agent, or Firm* — Morgan, Lewis & Bockius LLP (57) ABSTRACT

An apparatus for sterilizing an interior of a vehicle using a drone, may include a drone body of the drone and including a conformation sensor; one or more propellers coupled to the drone body; a UV unit coupled to the drone body and configured to radiate UV light; a sterilizer spray unit mounted to the drone body and configured to spray a sterilizer through the propeller; and a controller electrically connected to the UV unit or the sterilizer and configured to set a flight route in a vehicle, determine an infected region in the set flight route, and operate the UV unit or the sterilizer unit in correspondence to the infected region.

18 Claims, 6 Drawing Sheets

(51) Int. Cl.
*A61L 2/22* (2006.01)
*B64D 1/18* (2006.01)
*B64D 47/02* (2006.01)
*B64F 5/40* (2017.01)
*B64U 30/299* (2023.01)
*B64U 50/14* (2023.01)
*B64U 101/29* (2023.01)
*G02B 5/08* (2006.01)
*G02B 26/10* (2006.01)
*B64U 10/14* (2023.01)
*B64U 50/38* (2023.01)

(52) U.S. Cl.
CPC .............. *B64U 10/14* (2023.01); *B64U 50/38* (2023.01); *B64U 2101/29* (2023.01)

(56) References Cited

U.S. PATENT DOCUMENTS

| | | | |
|---|---|---|---|
| 2019/0055016 A1* | 2/2019 | Groninga | B64C 27/024 |
| 2019/0117812 A1* | 4/2019 | Olsen | A61L 2/26 |
| 2019/0216958 A1* | 7/2019 | Kreitenberg | A61L 2/24 |
| 2021/0299311 A1* | 9/2021 | Yu | B64U 50/19 |
| 2021/0308297 A1* | 10/2021 | Hassani | A61L 2/10 |
| 2021/0356958 A1* | 11/2021 | Rubæk | G05D 1/0022 |
| 2022/0120216 A1* | 4/2022 | Lee | F03D 15/05 |
| 2022/0143244 A1* | 5/2022 | Dietz | B64D 1/18 |
| 2023/0285618 A1* | 9/2023 | Rosen | A61L 2/10 |
| 2023/0302172 A1* | 9/2023 | Ohashi | A61L 2/10 |
| 2023/0310684 A1* | 10/2023 | Rister | B64F 5/30 |
| | | | 422/24 |

* cited by examiner

APPARATUS FOR STERILIZATION OF INSIDE OF VEHICLE USING DRONE

CROSS REFERENCE TO RELATED APPLICATION

The present application claims priority to Korean Patent Application No. 10-2020-0151536, filed on Nov. 13, 2020, the entire contents of which is incorporated herein for all purposes by this reference.

BACKGROUND OF THE INVENTION

Field of the Invention

The present invention relates to an apparatus for sterilizing an interior of a vehicle using a drone, and more particularly, the apparatus including a drone for sterilizing the interior of a vehicle, the apparatus being disposed in a vehicle and sterilizing an infected region in correspondence to a use condition.

Description of Related Art

In general, a drone, which is a flying object that is wirelessly controlled by an operator, was developed and used for military operations in the early stage, but recently, the application range is expanding to transportation, leisure, and industry.

Drones are used even in primary industries, such as agriculture, fishing, and livestock, to solve the problem that control of insect pests including spraying of agricultural chemicals and fertilizers is inefficiently performed on wide areas for a long time due to a lack of workers. Accordingly, controlling insect pests using a drone is spotlighted as the most practical and efficient system for solving the problems of a lack of manpower, cost, etc. in primary industries.

Furthermore, drones are used not only for controlling insect pests and spraying agricultural chemicals, but also in the technological field that performs sterilization, so technologies for using drones for various purposes are being currently developed.

Recently, technologies for improving the driving condition of vehicles using drones provided for the vehicles are being developed and technologies for performing unmanned flying of drones are being developed.

However, drones are disposed outside vehicles and used to receive information related to driving of the vehicles, and a drone configured to be operated in a vehicle has not been proposed. Furthermore, the demand for a device that is disposed in a vehicle to sterilize and disinfect the vehicle increases, and it is required to continuously manage infected regions that users continuously touch.

The information disclosed in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing an apparatus of sterilization of the interior of a vehicle using a drone to sterilize infected regions in the vehicle.

Various aspects of the present invention are to provide a drone that determines an infected region and performs sterilization in various ways.

The objectives of the present invention are not limited to those described above and other objectives not stated herein may be understood through the following description and may be made clear by embodiments of the present invention. Furthermore, the objectives of the present invention will be achieved by the configurations described in claims and combinations thereof.

To achieve the objectives of the present invention described above, an apparatus of sterilization of the interior of a vehicle using a drone includes the following configuration.

An apparatus of sterilization of the interior of a vehicle using a drone according to various exemplary embodiments of the present invention includes: a drone body of the drone and including a conformation sensor; one or more propellers coupled to the drone body; an ultraviolet (UV) unit coupled to the drone body and configured to radiate UV light; a sterilizer spray unit mounted to the drone body and configured to spray a sterilizer through the propeller; and a controller electrically connected to the UV unit or the sterilizer and configured to set a flight route in a vehicle, determine an infected region in the set flight route, and operate the UV unit or the sterilizer unit in correspondence to the infected region.

The UV unit may include: a UV radiator configured to radiate the UV light; a first rotor rotatably coupled to the drone body and configured to rotate the UV unit in a first direction with respect to the drone body by a first actuator coupled to the first rotor and the drone body and electrically connected to the controller; and a second rotor having the UV radiator and rotatably coupled to an end portion of the first rotor to rotate in a second direction perpendicular to the first direction by a second actuator coupling the first rotor and the second rotor and electrically connected to the controller.

The UV radiator may include: a reflector disposed on a side of the second rotor; a UV LED radiating the UV light to the reflector; and a horizontal mover mounted inside the second rotor, electrically connected to the controller, and selectively moving the UV LED in a width direction of the second rotor to change a distance between the UV LED and the reflector.

The controller may be configured to control the UV LED to be positioned away from the reflector such that a region irradiated by the UV radiator is increased.

The apparatus may further include an optical cable unit coupled to the second rotor and having a first end portion positioned to surround the reflector and a second end portion receiving the UV light radiated from the UV LED.

The optical cable unit may include: a tube through which the UV light radiated from the UV radiator travels; a first cable at least partially disposed on upper and lower external surfaces of the tube to move the optical cable up and down; and a second cable at least partially disposed on sides of the tube to move the tube left and right.

The first cable may be configured to apply up-down-directional tension to the tube in accordance with operation of a first roller rotatably coupled to the second rotor of the optical cable unit and connected to an actuator.

The second cable may be configured to apply left-right-directional tension to the tube in accordance with operation of a second roller rotatably coupled to the second rotor of the optical cable unit and connected to an actuator.

The sterilizer spray unit may include: a sterilizer vessel disposed in the drone body and storing the sterilizer; an inflow channel configured to send the sterilizer supplied from the sterilizer vessel into the propeller; and a connection channel formed in a propeller rotation shaft to which the one or more propellers are rotatably coupled such that the inflow channel and the sterilizer vessels are fluidically connected to supply the sterilizer.

The apparatus may further include an O-ring disposed between the propeller rotation shaft and the propeller.

The propeller may include: a casing covering the propeller; and a purification filter disposed at an upper portion of the casing.

The controller may be configured to determine a motion of a user through the conformation sensor and determines the infected region according to the determined motion of the user.

The controller may learn and store an internal conformation of the vehicle by using the conformation sensor and may receive real-time conformation information in accordance with flight of the drone, setting the flight route of the drone.

According to various exemplary embodiments of the present invention, it is possible to achieve the following effects from the configuration, combination, and operation relationship described below.

The present invention has an effect of providing a pleasant riding environment to passengers through a drone providing various sterilization methods.

The present invention has an effect of improving the use environment for a user by providing a sterilization method of automatically sterilizing an infected region using a drone.

The present invention has an effect of providing a sterilization method that can selectively perform intensive sterilization, depending on infected regions.

The methods and apparatuses of the present invention have other features and advantages which will be apparent from or are set forth in more detail in the accompanying drawings, which are incorporated herein, and the following Detailed Description, which together serve to explain certain principles of the present invention.

It may be understood that the appended drawings are not necessarily to scale, presenting a somewhat simplified representation of various features illustrative of the basic principles of the present invention. The specific design features of the present invention as included herein, including, for example, specific dimensions, orientations, locations, and shapes will be determined in part by the particularly intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the present invention(s) will be described in conjunction with exemplary embodiments of the present invention, it will be understood that the present description is not intended to limit the present invention(s) to those exemplary embodiments. On the other hand, the present invention(s) is/are intended to cover not only the exemplary embodiments of the present invention, but also various alternatives, modifications, equivalents and other embodiments, which may be included within the spirit and scope of the present invention as defined by the appended claims.

Hereinafter, embodiments of the present invention will be described in detail with reference to the accompanying drawings. Embodiments of the present invention may be modified in various ways and the scope of the present invention may not be construed as being limited to the embodiments to be described below. The embodiments are provided to more completely explain various exemplary embodiments of the present invention to those skilled in the art.

Terms '~er', '~unit', etc. used herein mean the units for processing at least one function or operation and may be implemented by hardware, software, or a combination of hardware and software.

Furthermore, the term '~sensor' described herein may be understood as a lower concept of the sensor unit described in claims.

Hereinafter, embodiments are described in detail with reference to accompanying drawings, and in the following description of the accompanying drawings, like reference numerals are provided to like components and repetitive description is omitted.

The present invention relates to an apparatus of sterilization of the interior of a vehicle using a drone 100, to control of flight of a drone 100 that determines an infected region and intensively sterilizes the infected region on the basis of interactive communication between a vehicle controller disposed in a vehicle and a controller 200 disposed in the drone 100.

An infected region is determined on the basis of the number of times of input to the vehicle controller through a switch, the number of times of movement of a user measured by a conformation sensor of the drone 100, etc.

The drone 100 may be docked to the overhead console of a vehicle and may be configured to charge a battery thereof with power from the vehicle. When designated flight of the drone 100 in a vehicle is finished, the drone 100 is controlled to return to the docking position. Furthermore, the drone 100 may be disposed at any position in a vehicle and is connected to the vehicle wirelessly or through a wire so that power is supplied to the drone 100.

The drone 100 and a vehicle controller may be configured to operate with each other, so wireless communication connection is possible between the vehicle controller disposed in a vehicle and the controller disposed in the drone 100.

The drone 100 may be provided from the outside of a vehicle, so when the drone 100 is provided from the outside of a vehicle, a vehicle controller is configured to open a window or a sunroof of the vehicle so that the drone 100 can enter the vehicle. When the drone 100 intensively sterilizes a vehicle at the outside, the drone 100 with a sterilization logic finished flies outside the vehicle in the same way.

Figure 1:
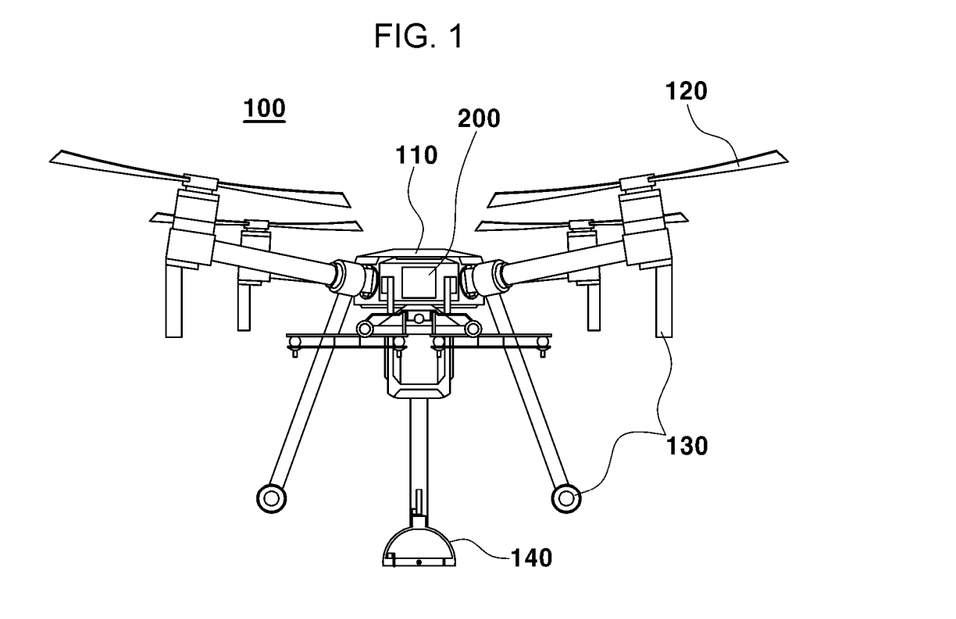
FIG. 1 is a view showing an apparatus of sterilization of the interior of a vehicle using a drone as various exemplary embodiments of the present invention.

FIG. 1 is a view showing the configuration of a drone 10, including combination relationships for determining an infected region and intensively sterilizing the infected region.

The drone 100 in various exemplary embodiments of the present invention may be disposed in a vehicle. The drone 100 includes a drone body 110, propellers 121, conformation sensors 130 disposed at the lower end portion of the drone body 110 and sides adjacent to the propellers 121, a communication unit receiving motion data of a user from a vehicle controller, a sterilizer distribution unit disposed in the drone body 110, and a UV unit 140.

The controller 200 of the drone 100 in various exemplary embodiments of the present invention is configured to store indoor data of a vehicle measured by the conformation sensors 130, to set a flight route of the drone 100 on the basis of the stored data, and to receive real-time data from the conformations sensors 130 to cope with changes of a conformation or passengers.

The conformation sensors 130 may include one or more LiDARs or radars disposed at the lower end portion of the drone 100 and one or more ultrasonic sensors disposed on the side of the drone 100.

The controller 200 on the drone 100 is configured to communicate with a vehicle controller and receive data about whether there is a passenger in the vehicle, and the operation position and the number of operation times of a switch by a passenger. The controller 200 of the drone 100 is configured to measure motions of a user, the time when the user touches the interior of a vehicle, and the number of times of touches using the conformation sensors 130, being able to determine infected regions. The controller 200 of the drone 100 may set an infected region by determining the number of operation times of a switch by a passenger and may set a flight route of the drone 100 to the determined infected region in cooperation with a vehicle controller. It is possible to execute a sterilization logic using at least one of the UV unit 140 or a sterilizer application unit to perform intensive sterilization.

In various exemplary embodiments of the present invention, an infected region is determined in a process of sterilizing the interior of a vehicle through the drone 100 and an area where there is a motion of a user is determined as an infected region through the conformation sensors 130 on the drone 100. A vehicle controller is configured to receive switch input or operation input of the vehicle and the controller 200 is configured to determine an infected region independently or in cooperation with the vehicle controller on the basis of a motion of a user measured through the conformation sensors 130.

The controller 200 sets an area in which a motion of a user exceeds a stored reference motion as an infected region.

In another exemplary embodiment of the present invention, it is possible to determine an area where there is a motion of a user through the conformation sensors 130 of the drone 100 or an area there is operation (switch) input by the controller 200 as an infected region.

When the contamination level of an infected region exceeds a reference value stored in the controller 200, it is possible to set a flight route of the drone 100 to perform sterilization through the UV unit 140. Alternatively, it is possible to set a flight route of the drone 100 by the controller 200 such that the sterilizer spreading unit of the drone 100 is operated. In various exemplary embodiments of the present invention, the controller 200 may be configured to simultaneously or separately operate the UV unit 140 and the sterilizer application unit.

In various exemplary embodiments of the present invention, the controller 200 is configured to perform intensive sterilization using a sterilizer spray unit 120 when an infected region is a reference area or wider, and to perform intensive sterilization using the UV unit 140 when an infected region is narrower than the reference area.

When there is a passenger, the controller 200 determines the position of the passenger using the conformation sensors 130 or a vehicle sensor, and controls the drone 100 such that the flight route is set not to influence the safety of the passenger when performing intensive sterilization. The controller 200 may compensate for the radiation height of the UV unit 140 and limits the sterilizer spray range in the area where there is a passenger.

The UV unit 140 is coupled to the drone body 110 through a connecting rod 141 and includes a first rotor 142 configured to rotate in the left-right of the drone body 100 (in a first direction) at an end portion of the connecting rod 141. A second rotor 143 including a UV radiator 144 is disposed at an end portion of the first rotor 142. The second rotor 143 is configured such that the UV radiator 144 is rotated I the up-down direction of the drone body 110 (in a second direction). The first rotor 142 and the second rotor 143 may be configured such that the UV radiator 144 is rotated in two axial directions perpendicular to each other.

The UV radiator 144 include a reflector 145 configured such that light emitted from a UV LED 146 travels out of the UV unit 140. The reflector 145 has a conical or elliptical cross-section and is configured such that the light emitted from the UV LED 146 spreads to a predetermined area. The reflector 145 is at least partially inserted into the second rotor 143 and faces the UV LED 146 disposed outside the second rotor 143. The UV LED 146 is moved in the width direction of the second rotor 143 by a horizontal mover 147 disposed in the second rotor 143 and the radiation region of the UV radiator 144 is changed by a change of the distance between the UV LED 146 and the reflector 145 fixed to the second rotor 143. Accordingly, the UV radiator 144 can provide an intensive sterilization function that sterilizes a relatively narrow area and a wide sterilization function that sterilizes a relatively wide area.

The UV radiator 144 of the UV unit 140 may be configured to rotate 360 degrees about the drone body 110 in the present way.

The sterilizer spray unit 120 has a sterilizer vessel 123 disposed in the drone body 110 and is controlled by the controller 200 such that a sterilizer in the sterilizer vessel 123 is sprayed to the propeller 121 through an opening.

The drone 100 determines an infected region transmitted from the controller 200 and the sterilizer is applied from the drone 100 flying over the infected region.

The sterilizer is sent to the propeller 121 through an inflow channel 126 formed in the propeller 121 and a connection channel 127 is formed between the sterilizer vessel 123 and the inflow channel 126 to supply fluid. The inflow channel 126 is longitudinally formed in the propeller 121 and the connection channel 127 is formed through a propeller rotation shaft 122 to be connected to the inflow channel 126 formed in the propeller 121 to supply fluid. The propeller 121 having the inflow channel 126 may be open at both end portions and may have one or more openings at the upper end portion or the lower end portion thereof such that the sterilizer flowing into the induction channel 126 is sprayed through the openings.

The sterilizer supplied into the inflow channel 126 may be discharged to both end portions of the propeller 121 by the rotational force of the propeller 121 and may be discharged to both end portions of the propeller 121 by a compressor 125 disposed in the sterilizer vessel 123.

Furthermore, purification filters 161 are disposed above the drone body 110 where the propellers 121 are disposed, at positions corresponding to the propellers 121. It is possible to determine the air quality inside a vehicle through a vehicle controller or the controller of the drone 100. When the air quality is a predetermined value stored in the controller 200 or lower, the air quality is improved by the purification filters 161 disposed in areas adjacent to the propellers 121 of the drone 100.

The controller 200 determines the air quality inside a vehicle on the basis of an air quality transmitted from the air conditioning system of the vehicle.

The purification filter 161 is disposed at the lower end portion of the propeller 121 to purify the air inside a vehicle in accordance with operation of the propeller 121. The controller 200 controls the drone 100 to turn or hover in a vehicle. In various exemplary embodiments of the present invention, the air quality does not mean only the amount of dust in the air, but means a measurement value including the amount of bacteria distributed in a vehicle.

A docking portion for docking with a vehicle may be disposed on the drone body 110 and is coupled and fixed to a station in a vehicle. A charging portion for charging the battery of the drone 100 through a wire or wirelessly may be disposed between the docking portion and the station.

Figure 2:
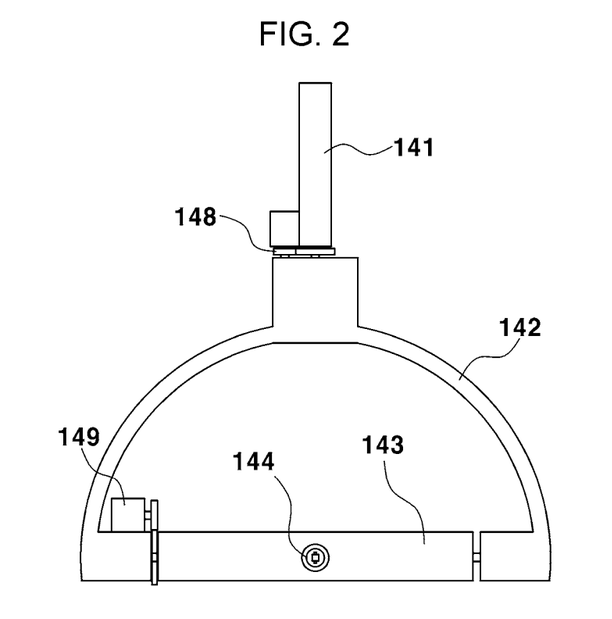
FIG. 2 is an enlarged view of a UV unit of the apparatus of sterilization of the interior of a vehicle using a drone as various exemplary embodiments of the present invention.
Figure 3:
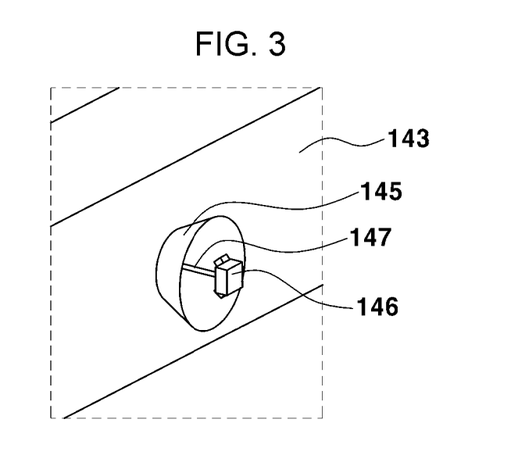
FIG. 3 is an enlarged view of a second rotor including a UV radiator as various exemplary embodiments of the present invention.
Figure 4A:
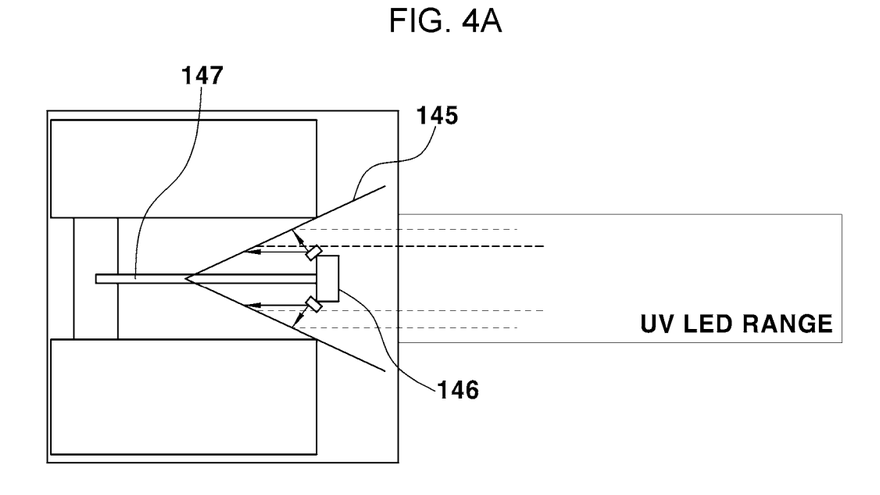
FIG. 4A is a side view of the second rotor having a narrow sterilization range through the UV radiator as various exemplary embodiments of the present invention.
Figure 4B:
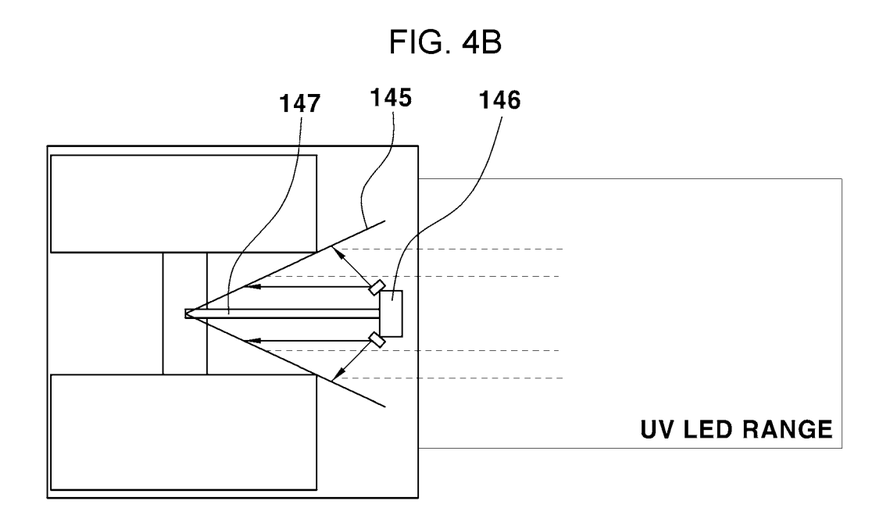
FIG. 4B is a side view of the second rotor having a wide sterilization range through the UV radiator as various exemplary embodiments of the present invention.

FIG. 2, FIG. 3 and FIG. 4B are enlarged view of the UV unit 140 according to various exemplary embodiments of the present invention.

The UV unit 140 is coupled to the drone body 110 through the connecting rod 141 and is rotated left and right with respect to the drone body 100 by a first actuator 148 disposed at the end portion of the connecting rod 141. The first actuator 148 is disposed at the connecting rod 141 to rotate gear unit on the rotational central axis of the UV unit 140, and the UV unit 140 and the gear unit can rotate together. The controller 200 applies the driving force of the first actuator 148 to control the amount of left-right rotation of the UV unit 140 in correspondence to an infected region in consideration of the flight state of the drone 100.

The second rotor 143 is coupled to an end portion of the first rotor 142 to rotate about both end portions of the first rotor 142. A second actuator 149 is disposed at an end portion of the second rotor 143 and fixed to the first rotor 142. The controller 200 controls the amount of rotation of the second rotor 143 through the second actuator 149.

That is, the first rotor 142 is controlled to rotate left and right about the perpendicular direction of the drone body 110 and the second rotor 143 is rotated up and down with respect to horizontal both end portions of the first rotor 142.

The UV radiator 144 is disposed on the second rotor 143 in the width direction of the second rotor 143 and includes the UV LED 146 emitting UV light and the reflector 145 reflecting the light from the UV LED 146 to the outside of the drone 100. The UV LED 146 has the horizontal mover 147 at an end portion to be configured to horizontally move in the width direction of the second rotor 143.

The horizontal mover 147 is configured to control the distance between the UV LED 146 and the reflector 145. The UV LED 146 is moved away from the reflector 145 to radiate UV light to a wide area and is moved close to the reflector 145 to radiate UV light to a narrow area.

FIG. 4A shows the radiation region of UV light when the horizontal mover 147 moves inside the second rotor 143 so that the UV LED 146 is positioned relatively close to the reflector and FIG. 4B shows the radiation region of UV light when the horizontal mover 147 moves maximally outwardly from the second rotor 143 so that the UV LED 146 is positioned relatively far away from the reflector 145.

As shown in the figures, when the controller 200 controls the horizontal mover 147 to move relatively far away from the reflector 145, the radiation region of UV light is large. Since the horizontal mover 147 is controlled by the controller 200, the distance between the UV LED 146 and the reflector 145 is changed in consideration of the area, etc., of an infected region.

Figure 5:
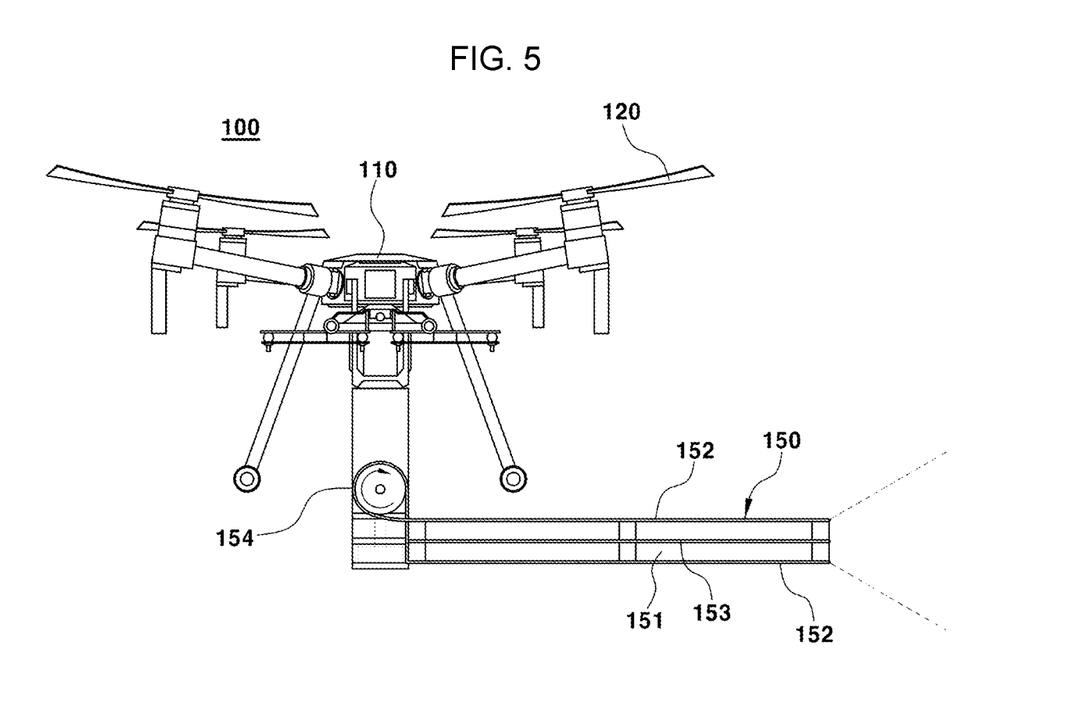
FIG. 5 is a view showing a drone including an optical cable unit as various exemplary embodiments of the present invention.
Figure 6A:
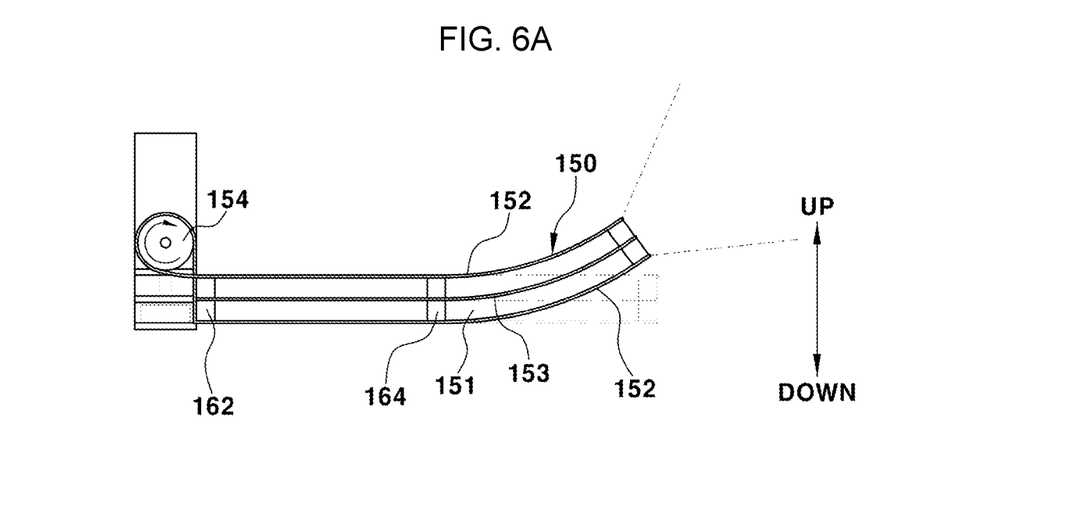
FIG. 6A shows the optical cable unit moving a tube up and down as various exemplary embodiments of the present invention.
Figure 6B:
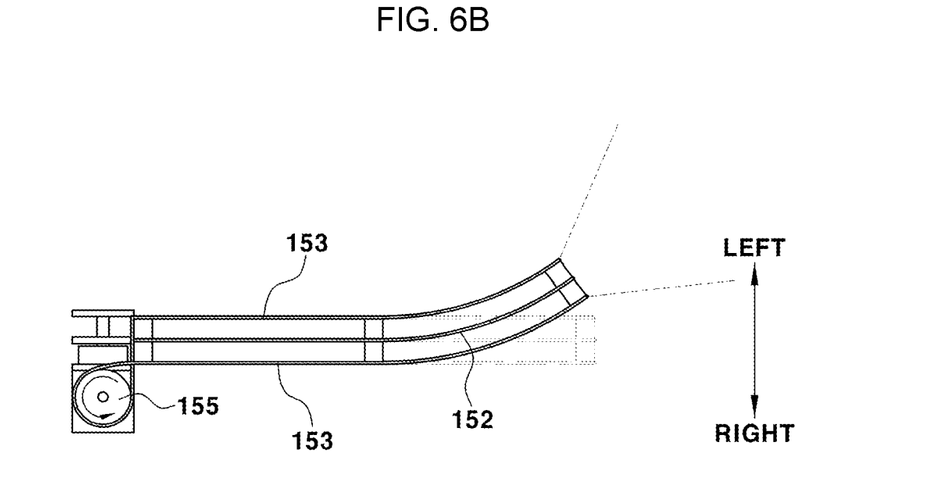
FIG. 6B shows the optical cable unit moving a tube left and right as various exemplary embodiments of the present invention.

FIG. 5 and FIG. 6B show an optical cable unit 150 fixed to the second rotor 143 as another exemplary embodiment of the present invention.

The optical cable unit 150 includes a tube 151 extending from the UV radiator 144, a first cable 152 at least partially disposed on the top portion and bottom portion of the tube 151 in the longitudinal direction of the tube 151, and a second cable 153 at least partially disposed on the side of the tube 151.

The first cable 152 has a first end portion coupled to a first roller 154 disposed adjacent to the second rotor 143 and a second end portion fixed to the end portion of the tube 151. The second cable 153 has a first end portion disposed adjacent to the second rotor 143 perpendicularly to the first roller 154 and a second end portion fixed to the end portion of the tube 151. The first cable 152 and the second cable 153 are spaced from each other to each have 90 degrees from the center axis of the tube 151.

The inside of the tube 151 has a light transmission property such that the UV light from the UV radiator 144 is transmitted to the end portion of the tube 151. The light transmission property of the inside of the tube 151 may be achieved by aluminum, Teflon, etc. Accordingly, the UV light from the UV radiator 144 can longitudinally travel through the tube 151.

As various exemplary embodiments of the present invention, the first cable 152 is wrapped around the first roller 154 and extends along the top portion and bottom portion of the tube 151.

As shown in FIG. 6A, when the first roller 154 is rotated in one direction, the cable on the top portion of the tube 151 is contracted and the cable on the bottom portion of the tube 151 is tensioned, whereby the end portion of the tube 151 is lifted up in the height direction. On the other hand, when the first roller 154 is rotated in another direction, the end portion of the tube 151 is moved downward.

As shown in FIG. 6B, the second cable 153 is wrapped around the second roller 155 and extends to the end portion of the tube 151 along the left and right sides of the tube 151. When the second roller 155 is rotated in one direction, the second cable 153 on the left side is contracted and the second cable 153 on the right side is tensioned, whereby the tube 151 is moved left. When the second roller 155 is rotated in another direction, the second cable 153 on the left side is tensioned and the second cable 153 on the right side is contracted, whereby the tube 151 is moved right.

The first cable 152 and the second cable 153 may be coupled to a cable route on the tube 151. The first cable 152 and the second cable 153 may be in contact with the external surface of the tube 151 in the region in which the cable route is disposed. According to the optical cable unit 150 including the cable route, the end portion of the tube 151 is moved with the first cable 152 and the second cable 153 in contact with the external surface of the tube 151 in correspondence to rotation of the first roller 154 and the second roller 155.

In an exemplary embodiment of the present invention, the tube 151 includes guide slots 157 and 159 to form the cable route and the first cable 152 and the second cable 153 are slidably coupled in the guide slots 157 and 159 respectively.

Figure 7:
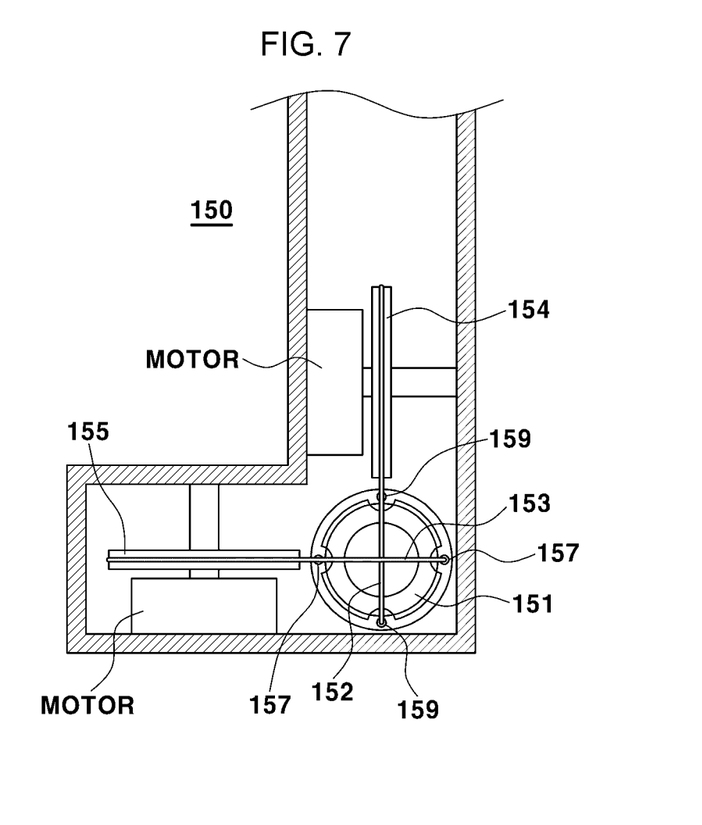
FIG. 7 shows the optical cable unit coupled to the second rotor as various exemplary embodiments of the present invention.

FIG. 7 shows a housing of the optical cable unit 150 coupled to the second rotor 143, including the first roller 154 and the second roller 155.

The optical cable unit 150 coupled to the second rotor 143 to transmit light from the UV radiator 144 to the end portion of the tube 151 includes a housing coupled to the second rotor 143. The tube 151 passes through the housing, and the first roller 154 and the second roller 155 respectively rotating the first cable 152 and the second cable 153 are disposed in the housing.

The first roller 154 and the second roller 155 are disposed to perpendicular to each other and each rotate in two directions. The first roller 154 may have the horizontal center axis of the drone body 110 and the second roller 155 may have a center axis disposed substantially in the same direction as the height direction of the drone body 110.

The first roller 154 controls the first cable 152 such that the end portion of the tube 151 is moved upwards in the height direction when the first roller 154 rotates in one direction and the second roller 155 controls the second cable 153 such that the end portion of the tube 151 is moved left with respect to the drone body 110 when the second roller 155 rotates in one direction.

The rotation amounts of the first roller 154 and the second roller 155 are selected in accordance with the flight route of the drone 100 and the position of an infected region to be sterilized. The tube 151 can radiate UV light to regions over which the drone 100 cannot fly, that is, over the cluster, steering wheel, etc. in a vehicle.

In an exemplary embodiment of the present invention, reinforcing members 162 and 164 are mounted to the tube 151 so that, while the reinforcing members 162 and 164 support a front portion of the tube 151, the remaining portion of the tube 151 having a free end can be freely bendable.

In an exemplary embodiment of the present invention, the first roller 154 and the second roller 155 are connected to motors electrically connected to the controller 200.

Figure 8:
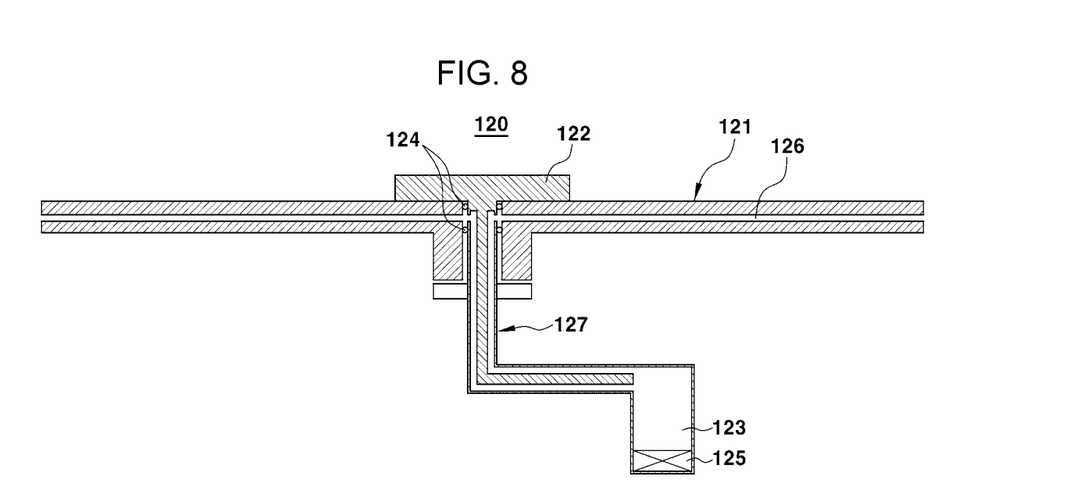
FIG. 8 shows a cross-section of a sterilizer spray unit as various exemplary embodiments of the present invention.

FIG. 8 is an enlarged view of the sterilizer spray unit 120.

A sterilizer is stored in the sterilizer vessel 123 in the drone body 110 and the stored sterilizer is sprayed to the interior of a vehicle through the opening of the propeller 121. The sterilizer vessel 123 is connected to the inflow channel 126 formed in the propeller 121 through the connection channel 127 formed through the propeller rotation shaft 122 to supply fluid.

The sterilizer may be moved to the inflow channel 126 from the sterilizer vessel 123 by the rotational force of the propeller 121 and may be sent to the inflow channel 126 of the propeller 121 by operation of the compressor 125 disposed in the sterilizer vessel 123 and electrically connected to the controller 200.

An O-ring 124 may be disposed between the propeller rotation shaft 122 and the propeller 121, whereby it is possible to prevent leakage of sterilizer between the propeller 121 that rotates and the propeller rotation shaft 122 that guides rotation of the propeller 121.

The inflow channel 126 disposed in the wing of the propeller 121 is connected to the connection channel 127 to supply fluid, and there may be no channel in other portions of the propeller 121 to prevent inflow of a sterilizer. Accordingly, it is possible to prevent a pressure drop of the sterilizer which is supplied into the inflow channel 126 of the propeller 121 from the sterilizer vessel 123.

Figure 9:
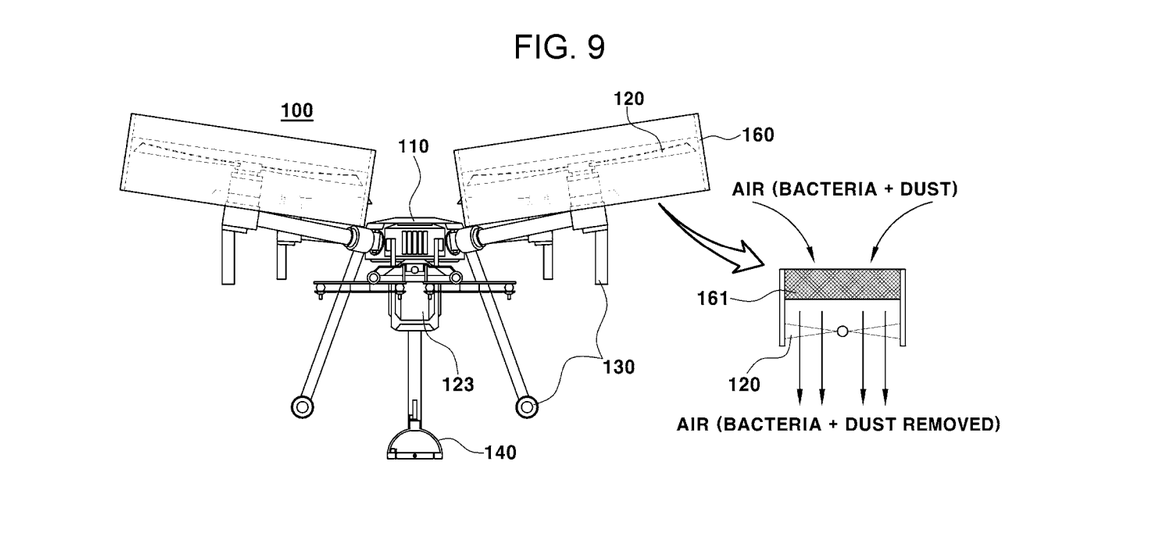
FIG. 9 is a view showing the configuration of a propeller including a purification filter as various exemplary embodiments of the present invention.

FIG. 9 shows the configuration of the purifier filter 161 disposed over the propeller 121 as another exemplary embodiment of the present invention.

One or more propellers 121 coupled to the drone body 110 each may be covered with a casing 160 fixed to a rod extending from the drone body 110. The casing 160 is positioned not interfere with rotation of the propeller 121 and is open up and down. The purification filter 161 is disposed at at least a portion of the upper end portion of the casing 160.

When the propeller 121 is rotated, air flows into the casing 160 from above. The inflow air passes through the purification filter 161 and is then discharged through the lower opening of the casing 160. Accordingly, the purification filter 161 can perform the function of purifying the air in a vehicle.

When it is determined that the air in a vehicle is contaminated, a vehicle controller or the controller 200 of the drone 100 may control the drone 100 to fly around or hover, and the air passing through the purification filter 161 may be purified through hovering.

The purification filter 161 is fixed in the casing 160 and when the UV unit 140 or the sterilizer spray unit 120 is operated, the purification function of the air in a vehicle is simultaneously performed.

Furthermore, the term related to a control device such as "controller", "control unit", "control device" or "control module", etc refers to a hardware device including a memory and a processor configured to execute one or more steps interpreted as an algorithm structure. The memory stores algorithm steps, and the processor executes the algorithm steps to perform one or more processes of a method in accordance with various exemplary embodiments of the present invention. The control device according to exemplary embodiments of the present invention may be implemented through a nonvolatile memory configured to store algorithms for controlling operation of various components of a vehicle or data about software commands for executing the algorithms, and a processor configured to perform operation to be described above using the data stored in the memory. The memory and the processor may be individual chips. Alternatively, the memory and the processor may be integrated in a single chip. The processor may be implemented as one or more processors. The processor may include various logic circuits and operation circuits, may process data according to a program provided from the memory, and may generate a control signal according to the processing result.

The control device may be at least one microprocessor operated by a predetermined program which may include a series of commands for carrying out the method disclosed in the aforementioned various exemplary embodiments of the present invention.

The aforementioned invention can also be embodied as computer readable codes on a computer readable recording medium. The computer readable recording medium is any data storage device that can store data which may be thereafter read by a computer system. Examples of the computer readable recording medium include hard disk drive (HDD), solid state disk (SSD), silicon disk drive (SDD), read-only memory (ROM), random-access memory (RAM), CD-ROMs, magnetic tapes, floppy discs, optical data storage devices, etc and implementation as carrier waves (e.g., transmission over the Internet).

In various exemplary embodiments of the present invention, each operation described above may be performed by a control device, and the control device may be configured by a plurality of control devices, or an integrated single control device.

In various exemplary embodiments of the present invention, the control device may be implemented in a form of hardware or software, or may be implemented in a combination of hardware and software.

For convenience in explanation and accurate definition in the appended claims, the terms "upper", "lower", "inner", "outer", "up", "down", "upwards", "downwards", "front", "rear", "back", "inside", "outside", "inwardly", "outwardly", "interior", "exterior", "internal", "external", "forwards", and "backwards" are used to describe features of the exemplary embodiments with reference to the positions of such features as displayed in the figures. It will be further understood that the term "connect" or its derivatives refer both to direct and indirect connection.

The foregoing descriptions of specific exemplary embodiments of the present invention have been presented for purposes of illustration and description. They are not intended to be exhaustive or to limit the present invention to the precise forms disclosed, and obviously many modifications and variations are possible in light of the above teachings. The exemplary embodiments were chosen and described to explain certain principles of the present invention and their practical application, to enable others skilled in the art to make and utilize various exemplary embodiments of the present invention, as well as various alternatives and modifications thereof. It is intended that the scope of the present invention be defined by the Claims appended hereto and their equivalents.

What is claimed is:

1. An apparatus for sterilizing an interior of a vehicle using a drone, the apparatus comprising:
   a drone body of the drone and including a conformation sensor;
   one or more propellers rotatably coupled to the drone body;
   an ultraviolet (UV) unit mounted to the drone body and configured to radiate UV light;
   a sterilizer spray unit mounted to the drone body and configured to spray a sterilant; and
   a controller electrically connected to the UV unit or the sterilizer spray unit and configured to set a flight route in a vehicle, to determine an infected region in the set flight route, and to operate the UV unit or the sterilizer spray unit in correspondence to the infected region,
   wherein the sterilizer spray unit includes:
   a sterilizer vessel disposed in the drone body and storing the sterilant;
   an inflow channel configured to send the sterilant supplied from the sterilizer vessel into at least one propeller among the one or more propellers; and
   a connection channel formed in a propeller rotation shaft to which the one or more propellers are rotatably coupled so that the inflow channel and the sterilizer vessels are fluidically connected to supply the sterilant through the connection channel.

2. The apparatus of claim 1, further including:
   a connecting rod to which the drone body is connected and to which the UV unit is rotatably connected; and
   an actuator coupling the connecting rod to the UV unit and electrically connected to the controller,
   wherein the UV unit is selectively rotated along a circumferential direction of the connecting rod by the actuator.

3. The apparatus of claim 1, wherein the UV unit includes:
   a UV radiator configured to radiate the UV light;
   a first rotor rotatably coupled to the drone body and configured to rotate the UV unit in a first direction with respect to the drone body by a first actuator coupled to the first rotor and the drone body and electrically connected to the controller; and
   a second rotor having the UV radiator and rotatably coupled to an end portion of the first rotor to rotate in a second direction perpendicular to the first direction by a second actuator coupling the first rotor and the second rotor and electrically connected to the controller.

4. The apparatus of claim 1, wherein the inflow channel is formed inside a body of at least one propeller among the one or more propellers in a longitudinal axis of the at least one propeller.

5. The apparatus of claim 1, further including an O-ring disposed between the propeller rotation shaft and the one or more propellers to surround a portion of the inflow channel.

6. The apparatus of claim 1, wherein at least one propeller of the one or more propellers includes:
   a casing covering the at least one propeller; and
   a purification filter disposed at a predetermined portion of the casing in the casing.

7. The apparatus of claim 1, wherein the controller is configured to determine a motion of a user through the conformation sensor and to determine the infected region according to the determined motion of the user.

8. The apparatus of claim 1, wherein the controller is configured to learn and to store an internal conformation of the vehicle by using the conformation sensor and to receive real-time conformation information in accordance with flight of the drone, setting the flight route of the drone.

9. An apparatus for sterilizing an interior of a vehicle using a drone, the apparatus comprising:
   a drone body of the drone and including a conformation sensor;
   one or more propellers rotatably coupled to the drone body;
   an ultraviolet (UV) unit mounted to the drone body and configured to radiate UV light;
   a sterilizer spray unit mounted to the drone body and configured to spray a sterilant; and
   a controller electrically connected to the UV unit or the sterilant and configured to set a flight route in a vehicle, to determine an infected region in the set flight route, and to operate the UV unit or the sterilizer unit in correspondence to the infected region,
wherein the UV unit includes:
   a UV radiator configured to radiate the UV light;
   a first rotor rotatably coupled to the drone body and configured to rotate the UV unit in a first direction with respect to the drone body by a first actuator coupled to the first rotor and the drone body and electrically connected to the controller; and
   a second rotor having the UV radiator and rotatably coupled to an end portion of the first rotor to rotate in a second direction perpendicular to the first direction by a second actuator coupling the first rotor and the second rotor and electrically connected to the controller, and
wherein the UV radiator further includes:
   a reflector disposed on a side of the second rotor;
   a UV light-emitting diode (LED) radiating the UV light to the reflector; and
   a horizontal mover mounted inside the second rotor, electrically connected to the controller, and selectively moving the UV LED in a width direction of the second rotor to change a distance between the UV LED and the reflector.

10. The apparatus of claim 9, wherein the horizontal mover selectively moves the UV LED in a direction perpendicular to a rotation axis of the second rotor to change the distance between the UV LED and the reflector.

11. The apparatus of claim 9, wherein the controller is configured to control the UV LED so that as the distance between the UV LED and the reflector is increased, a region irradiated by the UV radiator is increased.

12. The apparatus of claim 10, wherein the reflector is aligned to be inclined with an acute angle from a longitudinal axis of the horizontal mover and the UV LED is aligned to be oriented toward an inner surface of the reflector.

13. The apparatus of claim 9, further including an optical cable unit coupled to the second rotor and having a first end portion positioned to surround an end portion of the reflector and a second end portion receiving the UV light radiated from the UV LED.

14. The apparatus of claim 13, wherein the optical cable unit includes:
   a tube through which the UV light radiated from the UV radiator travels;
   a first cable at least partially disposed on upper and lower sides of the tube to move the optical cable up and down; and
   a second cable at least partially disposed on left and right sides of the tube to move the tube left and right.

15. The apparatus of claim 14, wherein the optical cable unit further includes at least a reinforcing member mounted to a portion of the tube so that, while the at least a reinforcing member supports a predetermined portion of the tube, a remaining portion of the tube having a free end is configured to be bendable.

16. The apparatus of claim 14, wherein the tube includes first and second guide slots along a longitudinal direction of the tube to form a cable route and the first cable and the second cable are slidably coupled in the first guide slot and the second guide slot respectively.

17. The apparatus of claim 14, wherein the first cable is configured to apply up-down-directional tension to the tube in accordance with operation of a first roller rotatably coupled to the second rotor of the optical cable unit and connected to an actuator electrically connected to the controller.

18. The apparatus of claim 14, wherein the second cable is configured to apply left-right-directional tension to the tube in accordance with operation of a second roller rotatably coupled to the second rotor of the optical cable unit and connected to an actuator electrically connected to the controller.

* * * * *